(12) United States Patent
Longo et al.

(10) Patent No.: US 9,345,466 B2
(45) Date of Patent: May 24, 2016

(54) SUTURE THREAD

(71) Applicant: ASSUT EUROPE S.P.A., Rome (IT)

(72) Inventors: Maurizio Longo, Rome (IT); Federica Scacchia, Teramo (IT); Francesco Lazzaro, Fossa (IT); Feliciano Crovella, Naples (IT)

(73) Assignee: ASSUT EUROPE S.P.A., Rome (IT)

( * ) Notice: Subject to any disclaimer, the term of this patent is extended or adjusted under 35 U.S.C. 154(b) by 0 days.

(21) Appl. No.: 14/266,635

(22) Filed: Apr. 30, 2014

(65) Prior Publication Data

US 2014/0236229 A1 Aug. 21, 2014

Related U.S. Application Data

(63) Continuation of application No. 13/807,922, filed as application No. PCT/IB2011/053016 on Jul. 7, 2011, now Pat. No. 8,747,438.

(30) Foreign Application Priority Data

Jul. 8, 2010 (IT) .............................. RM2010A0373

(51) Int. Cl.
*A61B 17/04* (2006.01)
*A61B 17/06* (2006.01)
*A61B 17/00* (2006.01)

(52) U.S. Cl.
CPC .............. *A61B 17/04* (2013.01); *A61B 17/0401* (2013.01); *A61B 17/06166* (2013.01); *A61B 17/06119* (2013.01); *A61B 2017/00526* (2013.01); *A61B 2017/0406* (2013.01); *A61B 2017/0417* (2013.01); *A61B 2017/0464* (2013.01); *A61B 2017/0619* (2013.01); *A61B 2017/06052* (2013.01); *A61B 2017/06176* (2013.01)

(58) Field of Classification Search
CPC ............. A61B 17/04; A61B 17/06166; A61B 17/0401; A61B 17/06119; A61B 2017/0464; A61B 2017/0619; A61B 2017/00526; A61B 2017/0417; A61B 2017/06176; A61B 2017/0406; A61B 2017/06052
USPC ................................... 606/222–225, 228–233
See application file for complete search history.

(56) References Cited

U.S. PATENT DOCUMENTS

| | | | | |
|---|---|---|---|---|
| 5,102,418 | A * | 4/1992 | Granger et al. | 606/224 |
| 6,506,197 | B1 * | 1/2003 | Rollero | A61B 17/0401 606/148 |
| 2003/0149447 | A1 * | 8/2003 | Morency et al. | 606/228 |
| 2004/0030354 | A1 * | 2/2004 | Leung | A61B 17/0401 606/232 |
| 2005/0267531 | A1 * | 12/2005 | Ruff et al. | 606/228 |
| 2006/0116718 | A1 * | 6/2006 | Leiboff | 606/228 |

FOREIGN PATENT DOCUMENTS

EP 2684527 A2 * 1/2014

* cited by examiner

*Primary Examiner* — Ashley Fishback
(74) *Attorney, Agent, or Firm* — Steinfl & Bruno LLP

(57) ABSTRACT

A suture thread having: a thread-shaped main body with spikes and a stopper cylinder having a diameter enlarged with respect to the main body is described.

6 Claims, 3 Drawing Sheets

SUTURE THREAD

CROSS REFERENCE TO RELATED APPLICATIONS

The present application is a U.S. Continuation Application of U.S. patent application Ser. No. 13/807,922 filed on Dec. 31, 2012, which in turn, is the U.S. National Stage of International Application PCT/IB2011/053016 filed on Jul. 7, 2011 which, in turn, claims priority to Italian Application RM2010A000373, filed on Jul. 8, 2010.

The present invention refers to a thread, especially for use as a suture thread.

The operation of surgical nature most frequently performed in operating room and outpatient clinic surgery is certainly that of suturing by thread. In spite of the frequency and the "historicity" of use of the suture threads, the in situ blocking modes of the ends thereof have not been optimized yet. In particular, in order to secure one end of the thread against a portion of biological tissue, the same thread is generally knotted on itself.

However, this blocking mode is intrinsically less than reliable as the knot, over time, tends to come undone; this entails that, for each suturing operation that proves necessary during surgery, the operator is forced to make a high number of knots in sequence. Therefore, the entire suturing operation carried out through the knotting technique requires a non-negligible time significantly affecting the total length of the intervention, with the associated consequences for the patient's well-being.

Therefore, the technical problem set and solved by the present invention is that of providing a thread—and in particular a suture thread—allowing to overcome the drawbacks mentioned above with reference to the known art.

Such a problem is solved by a thread according to claim 1.

Preferred features of the present invention are set forth in the dependent claims thereof.

The present invention provides some relevant advantages. The main advantage lies in the fact that the thread of the invention, by being equipped with a stopper included in correspondence of a longitudinal end of the thread itself, allows to reduce surgical times, eliminating the need to make plural knots, and concomitantly improving the reliability of the sutures, since the block is not subject to the drawback of coming undone. Moreover, by eliminating the need to knot the main body of the thread on itself, the invention allows a greater variety of choice for the rigidity level of the latter and for the materials of which it is made, thereby allowing to meet any type of suturing and surgery need.

Other advantages, features and operation steps of the present invention will be made apparent in the following detailed description of some embodiments thereof, given by way of example and not for limitative purposes. Reference will be made to the figures of the annexed drawings, wherein.

Figures 1, 1A:
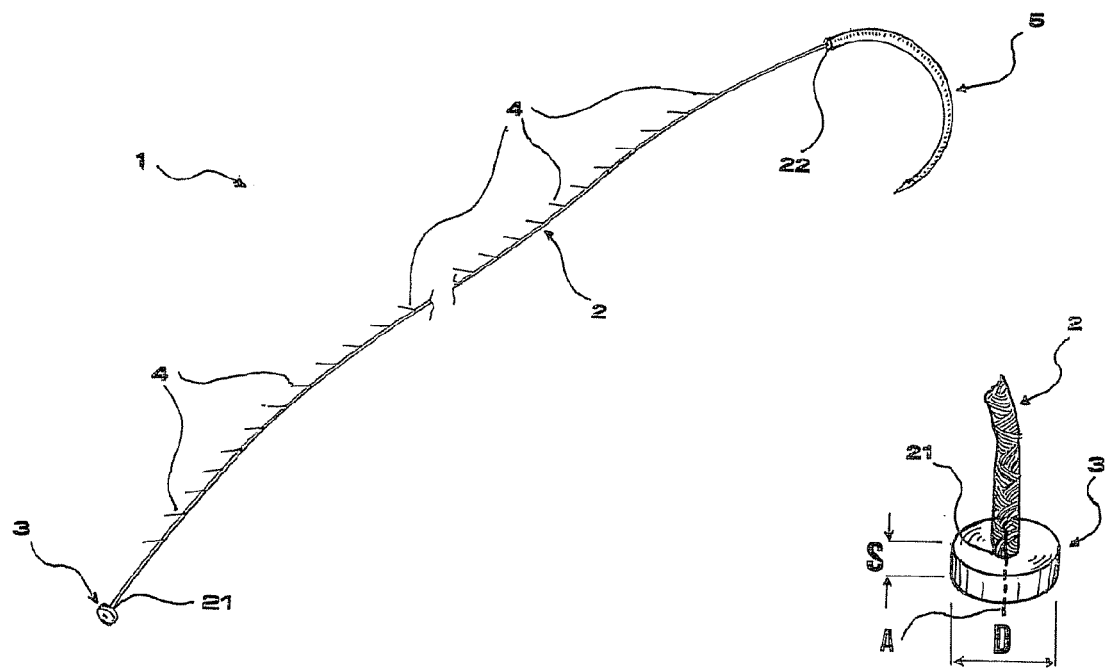
FIG. 1 shows a perspective view of a first preferred embodiment of the suture thread according to the present invention.
FIG. 1A shows an enlarged view of a detail of the thread of FIG. 1.

Referring initially to FIGS. 1 and 1A, a suture thread according to a first preferred embodiment of the invention is generally denoted by 1.

The thread 1 comprises first of all an elongated main body 2 having just a thread-like shape. The main body 2 is preferably flexible and extends, in a straight and extended configuration, along a longitudinal axis A.

On the main body 2 there are preferably provided a plurality of holding spikes 4, spaced out along substantially an entire length of the main body, where a distance from the suture needle to a closest holding spike of the plurality of holding spikes is less than said substantially entire length along which the plurality of holding spikes are spaced out i.e. thread portions arranged obliquely with respect to the prevalent direction of development of the main body 2 and apt, by virtue of said tilt, to engage the tissue sutured by the thread itself so as to prevent the unthreading of the latter along a given pull direction. Also the length and the thickness of the spikes 4 can be selected depending on the selected cutting tilt.

The spikes 4 can be applied on the main body 2 in a monolateral way, as in the depicted example, or in a plurilateral way. In both cases they can be manufactured in a monodirectional way, as in the depicted example, or in a pluridirectional way, i.e. have a tilt along a single direction or along plural divergent directions. Moreover, the spikes 4 can be applied on the main body 2 even along a helical path or a spiral-like path.

In correspondence of a first longitudinal end 21 of the main body 2, the thread 1 provides a stopper 3 having a section enlarged with respect to the main body 2 itself.

Preferably, the stopper 3 has a substantially cylindrical shape, preferably with an axis of the cylinder aligned with the axis A of the main body 2.

Always according to a preferred embodiment, the stopper 3 has a diameter D of about 4 mm and a thickness S comprised in a range of about 1-2 mm.

Figure 3:
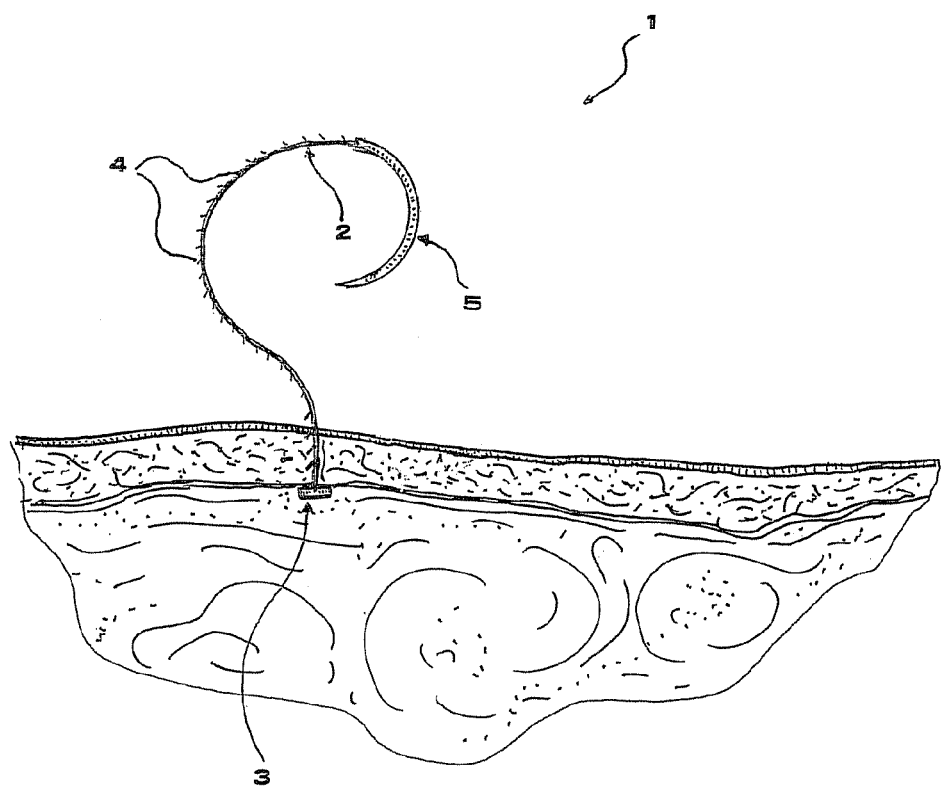
FIG. 3 shows a perspective view of the suture thread of FIG. 1, in use during surgery.

During suturing, and as shown in FIG. 3, the stopper 3, by virtue of its own section enlarged with respect to the main body 2, can block the corresponding longitudinal end 21 of the latter in abutment against a tissue flap.

Main body 2 and stopper 3 can be made both of a same material and of different materials, preferably of absorbable synthetic type.

In the present example, the stopper 3 and/or the main body 2 can be made of a material selected from a group comprising: glycolide polymer (PGA), copolymer of glycolide and lactide (PGLA), Poly(p-dioxanone) (PDO), copolymer of glycolide and epsilon-caprolactone (PGCL), and copolymer of Poly(l-lactide) and epsilon-caprolactone P(LA-CL).

The stopper 3 can be fixed to the main body 2 by heat-sealing.

Figure 4A:
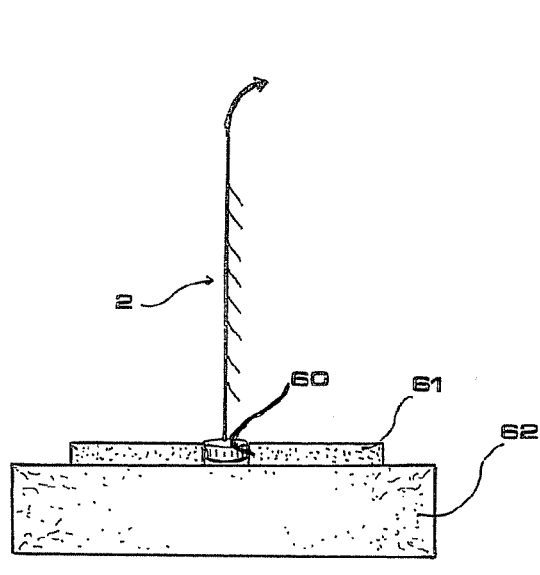
FIGS. 4A, 4B and 4C show schematic front views illustrating three respective steps of a preferred method for manufacturing the suture thread of FIG. 1.
Figure 4B:
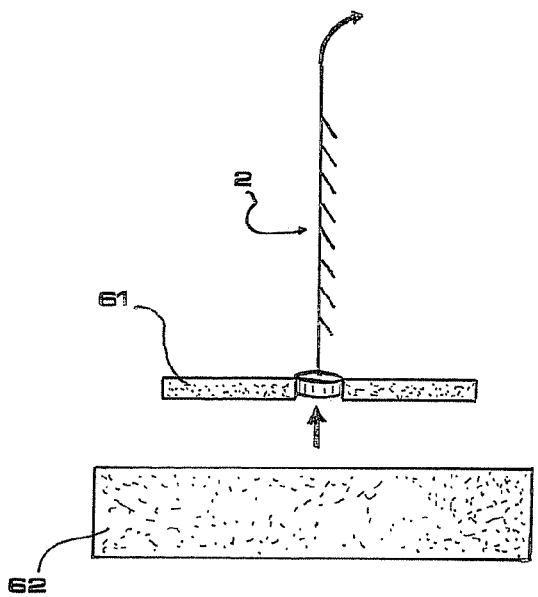
Figure 4C:
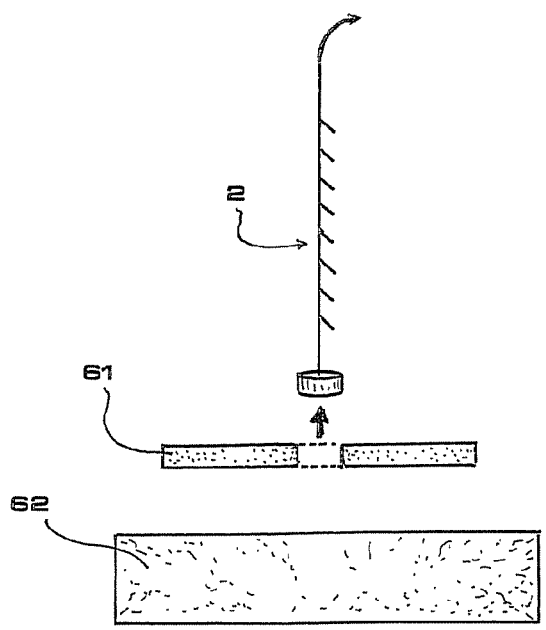

In particular, a preferred embodiment schematically illustrated in FIGS. 4A, 4B and 4C envisages that the stopper 3 be made by melting of poly(p-dioxanone) polymer in suitable moulds 60 of cylindrical shape of the above-mentioned dimensions, preferably made in the form of openings shaped on a metal plate 61 resting on a board 62 heated to about 130° C.

The connection between stopper 3 and main body 2 is then obtained by the following steps:

sealing of the "free" end 21 of the thread into the polymer paste still molten in the mould 60 (the correct positioning of the thread at the center of the cylindrical element can be guaranteed by a truing device positioned on the plate 61)—this step is schematically shown in FIG. 4A;

removing the metal plate 61 from the heated board 62, in order to obtain the cooling of the plate itself—this step is schematically shown in FIG. 4B; and separating the stopper from the metal plate—this step is schematically shown in FIG. 4C.

Advantageously, the thread 1 is then prearranged, in correspondence of a second longitudinal end 22 of the main body 2 opposite to that associated to the stopper 3, with a suture needle 5 having a substantially straight or curved shape. Such a needle can be made of stainless steel (e.g. AISI 300 series or AISI 400 series).

Figure 2:
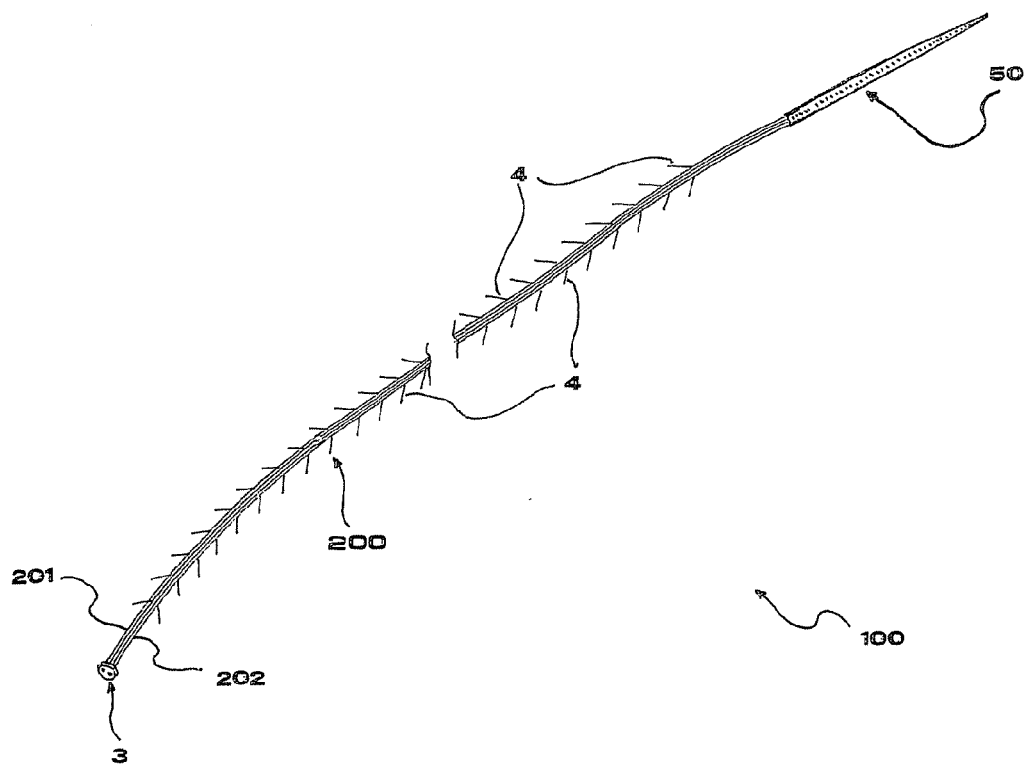
FIG. 2 shows a perspective view of a second preferred embodiment of the suture thread according to the present invention.

According to a second preferred embodiment shown in FIG. 2, a suture thread, denoted herein by 100, has a main body, denoted herein by 200, which comprises a pair of thread-shaped members 201, 202, apt to define a generally ring-shaped or loop-like structure of the thread itself. The spikes 4 are arranged substantially symmetrically along each of thread-shaped member 201, 202 of the pair.

The thread 100 comprises a stopper 3 analogous to that already described above, and in this case as well it is prearranged with a suture needle, here substantially straight, denoted by 50.

It will be understood that a plurality of suture threads, each as described above with reference to FIGS. 1 and 2, may be provided in various calibers, preferably comprised in the range USP 6/0-8, and in various lengths.

It will also be understood that a plurality of suture threads, each as described above with reference to FIGS. 1 and 2, may be provided in the form of a reel. In particular, in that case threads will be arranged in a longitudinal sequence and removably connected in correspondence of respective ends.

It will be understood that although the invention has been described with specific reference to suture applications, it can advantageously be used for any type of surgical need in which the use of a thread to be blocked in situ be required.

Moreover, in a broader meaning the invention can find application also in a field different from the surgical one, for instance that of threads for sewing, especially in specialized fields like those of sewing or stitching technical fabrics, such as for use in fishing, motorcycling, etc.

The present invention has been hereto described with reference to preferred embodiments thereof. It is understood that other embodiments might exist, all falling within the concept of the same invention, as defined by the protective scope of the claims hereinafter.

The invention claimed is:

1. A thread for suture or other sewing or stitching applications, comprising:
    an elongated main body comprising a pair of thread-shaped members;
    a stopper having a section enlarged with respect to said main body,
    wherein said stopper has a substantially cylindrical shape having one free circular face and one opposite circular face attached to one end of each of the thread-shaped members, a suture needle having a substantially straight or curved shape attached to the pair of thread-shaped members at a longitudinal end opposite of that associated with said stopper
    wherein said stopper has a thickness along said cylinder axis comprised in a range of about 1-2 mm,
    wherein said stopper has a diameter of about 4 mm,
    and wherein said stopper and said main body are made of a material selected from a group comprising: glycolide polymer (PGA), copolymer of glycolide and lactide (PGLA), Poly(p-dioxanone) (PDO), copolymer of glycolide and epsilon-caprolactone (PGCL),
    and copolymer of Poly(l-lactide) and epsilon-caprolactone P(LA-CL) and
    a plurality of holding spikes spaced out along substantially an entire length of the main body.

2. The thread according to claim 1, wherein said holding spikes are arranged on said main body in a monolateral way, in a plurilateral way and/or along a helical path.

3. The thread according to claim 1, wherein said holding spikes are arranged on said main body in a monodirectional or pluridirectional way.

4. The thread according to claim 1, wherein said stopper is fixed to said main body by heat-welding.

5. The thread according to claim 1, wherein the spikes along each of thread-shaped member of the pair are arranged substantially symmetrically along a direction of the longitudinal development of said main body.

6. The thread according to claim 1, wherein a distance from the suture needle to a closest holding spike of the plurality of holding spikes is less than said substantially entire length along which the plurality of holding spikes are spaced out.

* * * * *